United States Patent [19]
Prasad et al.

[11] Patent Number: 5,831,112
[45] Date of Patent: Nov. 3, 1998

[54] PROCESS FOR PRODUCING STABLE, LOW ODOR S,S,S-TRIBUTYLPHOSPHOROTHRITHIOTE

[75] Inventors: Vidyanatha A. Prasad, Leawood, Kans.; Peter E. Newallis, Pittsburgh, Pa.

[73] Assignee: Bayer Corporation, Pittsburgh, Pa.

[21] Appl. No.: 878,857

[22] Filed: Jun. 20, 1997

Related U.S. Application Data

[63] Continuation-in-part of Ser. No. 705,456, Aug. 29, 1996, abandoned, which is a continuation-in-part of Ser. No. 494,498, Jun. 26, 1995, abandoned.

[51] Int. Cl.[6] .................................................. C07F 9/17
[52] U.S. Cl. ........................... 558/146; 558/149; 558/208
[58] Field of Search ....................... 558/146, 149

[56] References Cited

U.S. PATENT DOCUMENTS

| | | | |
|---|---|---|---|
| 2,943,107 | 6/1960 | Rattenbury et al. | 260/461 |
| 5,183,916 | 2/1993 | Zakaryan et al. | 558/95 |
| 5,189,195 | 2/1993 | Newallis et al. | 558/208 |

*Primary Examiner*—Michael G. Ambrose
*Attorney, Agent, or Firm*—Joseph C. Gil; Carol Marmo

[57] ABSTRACT

The invention is directed to a process for producing a stable, low odor S,S,S-tributylphosphorotrithioate having a level of dibutyl disulfide of 0.3% by weight or less. The process broadly includes the steps of a) reacting S,S,S-tributylphosphorotrithioite with an oxidizing agent to produce a crude S,S,S-tributylphosphorotrithioate, b) treating the crude product with sodium bisulfite to decompose any excess oxidizing agent, c) adding a caustic solution having a caustic concentration of from 25 to 50% by weight directly to the reaction mixture of step b), the addition of said caustic solution being stopped once the total caustic concentration is less than 10% by weight and once the pH is constant, and d) phase separating S,S,S-tributylphosphorotrithioate from the mixture of step c).

4 Claims, No Drawings

PROCESS FOR PRODUCING STABLE, LOW ODOR S,S,S-TRIBUTYLPHOSPHOROTHRITIOTE

This application is a continuation-In-part of U.S. application Ser. No. 08/705,456, filed Aug. 29, 1996, now abandoned, which in turn was a continuation-in-part of U.S. application Ser. No. 08/494,498, filed Jun. 26, 1995, now abandoned.

BACKGROUND OF THE INVENTION

1. Field of Invention

The present invention relates to a process for producing storage-stable, low odor S,S,S-tributylphosphorotrithioate.

2. Brief Description of the Prior Art

Generally, the process for producing S,S,S-tributylphosphorotrithioate is known in the art. It can be produced by reacting phosphorus trichloride with butyl mercaptan and then oxidizing this reaction product. A by-product formed when unreacted butyl mercaptan is oxidized is the highly odorous dibutyl disulfide. Dibutyl disulfide is also a by-product formed upon the decomposition of trace amounts of S,S,S-tributylphosphorotrithioate. The decomposition occurs during the oxidation of S,S,S-tributylphosphorotrithioite to form S,S,S-tributylphosphorotrithioate.

In an effort to reduce the odor problems associated with dibutyl disulfide, several approaches have been taken to reduce levels of the same formed during the production process, and the levels of dibutyl disulfide present in the final product—S,S,S-tributylphosphorotrithioate. In one approach, S,S,S-tributylphosphorotrithioite (the intermediate from which S,S,S-tributylphosphorotrithioate is produced) is prepared by reducing the amount of butyl mercaptan used. See, for example, U.S. Pat. No. 2,943,107. In another approach, the phosphorus trichloride and a slight excess of butyl mercaptan are added simultaneously to a reaction vessel maintained at the reaction temperature. See U.S. Pat. No. 5,183,916.

In each of these approaches, however, there is still some unreacted butyl mercaptan which oxidizes to form the odorous dibutyl disulfide. The odor problem is compounded when crude S,S,S-tributylphosphorotrithioate is treated with an alkaline material to remove certain impurities that can adversely affect the stability of the final S,S,S-tributylphosphorotrithioate. During the treatment (hydrolysis) of the crude S,S,S-tributylphosphorotrithioate with the alkaline material, a finite amount of dibutyl disulfide, which is undesirable, is formed. If the hydrolysis conditions are not carefully controlled, additional dibutyl disulfide is formed due to the decomposition of the S,S,S-tributylphosphorotrithioate.

U.S. Pat. No. 5,189,195 discloses a process for producing a stable S,S,S-tributylphosphorotrithioate having reduced levels of the odorous by-product dibutyl disulfide. In the process described, crude S,S,S-tributylphosphorotrithioate was prepared by first reacting phosphorous trichloride with butyl mercaptan. The resultant S,S,S-tributylphosphorotrithioite was then oxidized. Excess oxidizing agent was then decomposed by adding sodium bisulfite. The crude S,S,S-tributylphosphorotrithioate was then separated from the aqueous phase. A caustic solution having a concentration of less than 10% was then added to the crude S,S,S-tributylphosphorotrithioate until the pH remained constant (see column 2, line 61 through column 3, line 10). After the hydrolysis step, another phase separation was carried out in order to isolate the product.

The present invention provides an improved process for producing stable and low odor S,S,S-tributylphosphorotrithioate.

SUMMARY OF THE INVENTION

In accordance with the foregoing, the present invention encompasses a process for producing a stable, low odor S,S,S-tributylphosphorotrithioate having a reduced level of dibutyl disulfide comprising: reacting S,S,S-tributylphosphorotrithioite with an oxidizing agent to produce a mixture containing the crude S,S,S-tributylphosphorotrithioate; treating the mixture with sodium bisulfite; treating the mixture with an effective concentration of a caustic solution to phase separate the crude S,S,S-tributylphosphorotrithioate and stabilize the S,S,S-tributylphosphorotrithioate in its final form; the effective concentration is provided by a combination of a high concentration of the caustic solution and water that is present in the mixture after the reaction with the oxidizing agent. By "crude S,S,S-tributylphosphorotrithioate" is meant a reaction mixture that is obtained by oxidizing S,S,S-tributylphosphorotrithioite derived from the reaction of phosphorous trichloride with butyl mercaptan.

The advantages of this process reside in: distinctly harnessing some of the commonly used reactants to improve the process, eliminating the use of other commonly used reactants and eliminating some of the commonly used process steps. Specifically, one of the advantages of the process resides in the use of commercially available 50% sodium hydroxide in combination with water present in aqueous hydrogen peroxide as a diluent for the high concentration of sodium hydroxide. This eliminates the need for a dedicated caustic tank containing a specified concentration of a caustic solution (such as a 5 to 10% caustic solution). Another key advantage of the process resides in the elimination of a phase separation step following the addition of the sodium bisulfite. Yet another advantage of the process resides in the elimination of most of the aqueous waste stream that is produced during production requiring two phase separations. These and other aspects of the invention are described more fully hereunder.

DETAILED DESCRIPTION OF THE INVENTION

More particularly, the present invention is directed to a process for producing a stable, low odor S,S,S-tributylphosphorotrithioate having a level of dibutyl disulfide of 0.3% by weight or less comprising:

a) reacting S,S,S-tributylphosphorotrithioite with an oxidizing agent to produce a crude S,S,S-tributylphosphorotrithioate, b) treating the crude product with sodium bisulfite to decompose any excess oxidizing agent, c) adding a caustic solution having a caustic concentration of from 25 to 50% by weight directly to the reaction mixture of step b), the addition of said caustic solution being stopped once the total caustic concentration is less than 10% by weight and once the pH is constant, and d) phase separating S,S,S-tributylphosphorotrithioate from the mixture of step c).

The present invention therefore relates to an improved process for producing stable, low odor S,S,S-tributylphosphorotrithioate by using a high concentration of a caustic solution as a starting material to provide an effective 5 to 10% concentration of the caustic solution to phase-separate crude S,S,S-tributylphosphorotrithioate and stabilize the same in its final form. The effective concentration is provided in-situ, by a combination of a high concentration of caustic solution with the mixture containing the crude S,S,S-tributylphosphorotrithioate and water. The water in the reaction mixture can be provided by an aqueous composition of an oxidizing agent that is used to convert S,S,S-tributylphosphorotrithioite to the crude S,S,S-tributylphosphorotrithioate. The water can also be provided by water of reaction that is obtained when, for instance, hydrogen peroxide is used as the oxidizing agent (hydrogen peroxide is itself reduced to water).

The crude S,S,S-tributylphosphorotrithioate may be prepared by any of the techniques known to those skilled in the art. Illustratively, phosphorus trichloride is reacted with butyl mercaptan to produce S,S,S-tributylphosphorotrithioite. The butyl mercaptan is generally used in excess. This reaction is generally carried out at a temperature of from about 90° to about 115° C. The S,S,S-tributylphosphorotrithioite thus formed is then oxidized with an oxidizing agent to form a mixture containing crude S,S,S-tributylphosphorotrithioate. Suitable oxidizing agents include: hydrogen peroxide, perborates and persulfates. To decompose any excess of the oxidizing agent, the mixture is treated with sodium bisulfite, generally in amount of from about 5 to about 10% by weight based on the amount of oxidizing agent used.

In accordance with this invention, a high concentration of caustic solution is employed as a starting material to isolate the S,S,S-tributylphosphorotrithioate and stabilize it in its final form. More specifically, the high concentration caustic solution is used in combination with the mixture containing the crude S,S,S-tributylphosphorotrithioate, sodium bisulfite and water. The amount and high concentration of the caustic solution is such as would combine with a mixture containing S,S,S-tributylphosphorotrithioate and water to attain an effective concentration of the caustic solution to produce via phase separation S,S,S-tributylphosphorotrithioate and reduced levels of dibutyl disulfide. The term "high concentration" is used herein to denote that one can employ the caustic solution as a starting material, in higher concentrations than those employed by the art-related processes. The concentration of the caustic solution can be from about 25 to 50% and preferably 45 to 50%. It is a distinct feature of the invention that where the caustic solution comprises sodium hydroxide, a readily available and high concentration of the sodium hydroxide solution can be obtained and used herein., Typically, a 50% concentration of sodium hydroxide is employed herein.

The effective concentration of the caustic solution can be obtained from a combination of the high concentration of the caustic solution with the mixture containing the crude S,S, S-tributylphosphorotrithioate and water. More specifically, the effective concentration can be obtained by adding the high concentration of the caustic solution to the reaction mixture containing water, in an amount sufficient to provide an effective concentration. Typically, the water is obtained from an aqueous solution of the oxidizing agent. Illustratively, hydrogen peroxide, the oxidizing agent, is commercially provided as a 35% aqueous solution. Additional water can be obtained after oxidation wherein hydrogen peroxide is reduced to water. The effective concentration should be below 10% by weight and preferably about 4 to 6% by weight. (This is governed and controlled by the amount of the high concentration caustic solution used.)

As the caustic solution, one can employ a solution of a strong alkali metal hydroxide, preferably sodium hydroxide in a high concentration. The caustic solution is added until the pH of the reaction mixture is constant. (The pH is generally about 9–11 at a temperature of about 60° C.) Where the caustic solution is sodium hydroxide, it is preferably added in an amount such that at least about 0.1 mole of sodium hydroxide will be present for each mole of crude S,S,S-tributylphosphorotrithioate being treated. The sodium hydroxide could be used in lesser amounts but such lesser amounts compromise the stability characteristics of the final phosphorotrithioate product or the ability to isolate the product via phase separation. It is also preferred that the sodium hydroxide not be used in quantities such that substantially more than 0.1 mole of sodium hydroxide is present for each mole of crude S,S,S-tributylphosphorotrithioate present. No additional improvement with respect to stability of the final product was obtained at higher usage levels. In addition, the final product contained increased quantities of the unwanted dibutyl disulfide.

The final product is recovered from the caustic/crude phosphorotrithioate mixture by standard techniques such as phase separations. It is a distinct feature of the invention that it eliminates one phase separation step and significantly reduces waste water that would otherwise be generated from the second phase separation. A distinct feature of the invention is that this process consists essentially of a single phase separation step. This reduces yield loss which is associated with processes involving multiple phase separations. The dibutyl disulfide level is reduced to or maintained at less than 0.30%, preferably to less than 0.10%. The product prepared by the process of the invention is useful as a cotton defoliant.

Having thus described our invention, the following examples are given as being illustrative thereof. All parts and percentages are parts and percentages by weight, unless otherwise indicated.

EXAMPLES

Example 1

The crude S,S,S-tributylphosphorotrithioate was prepared by adding one mole of phosphorus trichloride per 3.36 moles of butyl mercaptan to a reactor maintained at a temperature of about 115° C. in the presence of nitrogen for a period of 8 hours to form S,S,S-tributylphosphorotrithioite. After removal of as much of the excess butyl mercaptan as possible, the S,S,S-tributylphosphorotrithioite was oxidized by adding peroxide dropwise over a period of one hour to the reactor which was maintained at a temperature of from 30° to 32° C. This mixture was then heated to a temperature of about 41° C. and maintained at that temperature for one hour. Sodium bisulfite was then added to decompose any excess oxidizing agent.

400 gm. of the crude S,S,S-tributylphosphorotrithioate (i.e., containing water, the S,S,S-tributylphosphorotrithioate, and sodium bisulfite) was charged to a 500 ML erlenmeyer flask and agitated at 60° C. 6 gm of 50% sodium hydroxide was added dropwise to the flask until the pH of the resulting reaction mixture remained constant at 10. This mixture was then heated at a temperature of 60° C. with agitation for one hour and cooled to 55° C. Concentrated hydrochloric acid was then added until the pH remained constant at 4. The mixture was allowed to stand until the S,S,S-tributylphosphorotrithioate separated. The S,S,S-tributylphosphorotrithioate was then recovered and analyzed by gas chromatography. The results of this analysis were as follows:

| | |
|---|---|
| Dibutyl disulfide | 0.29% (water-free basis) |
| S,S,S-tributyl-phosphoro-trithioate | 99.7% (water-free basis) |
| BuSH (butyl mercaptan) | 0.072% (water-free basis) |

The storage stability of the product was monitored by measuring the levels of n-butylmercaptan in the product when maintained at a temperature of 60° C. in a constant temperature oven for a given period of time. The length of time for which the level of n-butylmercaptan remained constant is reported as the period for which the sample was storage stable. The S,S,S-tributylphosphorotrithioate thus obtained was storage stable for the entire test period of 21 days.

Example 2 (Comparative)

The examples of U.S. Pat. 5,189,195 require a phase separation step following the sodium bisulfite addition. As reported in the '195 patent, the amount of dibutyl disulfide ranged from as low as 0.21% to as high as 0.69% (see Table 1).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing a stable, low odor S,S,S-tributylphosphorotrithioate having a level of dibutyl disulfide of 0.3% by weight or less comprising:

a) reacting S,S,S-tributylphosphorotrithioate with an oxidizing agent to produce a crude S,S,S-tributylphosphorothioate, b) treating the crude product with sodium bisulfite to decompose any excess oxidizing agent, c) adding a caustic solution having a caustic concentration of from 25 to 50% by weight directly to the reaction mixture of step b), the addition of said caustic solution being stopped once the total caustic concentration is less than 10% by weight and once the pH is constant, and d) phase separating S,S,S-tributylphosphorotrithioate from the mixture of step C).

2. The process of claim 1 wherein the caustic solution is a sodium hydroxide solution.

3. The process of claim 1 wherein the sodium hydroxide is added in an amount such that about 0.1 mole of sodium hydroxide is present for each mole of crude S,S,S-tributylphosphorotrithioate.

4. The process of claim 1 in which the caustic solution is added until a constant pH of approximately 9 to 11 is attained.

* * * * *